United States Patent [19]
Matschke

[11] Patent Number: 5,874,741
[45] Date of Patent: *Feb. 23, 1999

[54] APPARATUS FOR GERMICIDAL CLEANSING OF WATER

[76] Inventor: Arthur L. Matschke, P.O. Box 599, Brookfield Center, Conn. 06804

[ * ] Notice: The term of this patent shall not extend beyond the expiration date of Pat. No. 5,612,001.

[21] Appl. No.: 796,724

[22] Filed: Mar. 3, 1997

Related U.S. Application Data

[63] Continuation-in-part of Ser. No. 538,447, Oct. 3, 1995, Pat. No. 5,612,001.

[51] Int. Cl.⁶ ........................................................ C02F 1/32
[52] U.S. Cl. ......................... 250/435; 422/24; 422/186.3; 422/905; 210/748; 250/438
[58] Field of Search ............................ 422/23, 24, 186.3, 422/905; 210/748; 250/432 R, 434, 436, 437, 455.11, 504 R, 455.1, 435, 438

[56] References Cited

U.S. PATENT DOCUMENTS

| | | |
|---|---|---|
| 4,661,264 | 4/1987 | Goudy, Jr. ............................. 422/24 X |
| 4,739,152 | 4/1988 | Downs . |
| 4,798,702 | 1/1989 | Tucker ...................................... 422/24 |
| 5,120,450 | 6/1992 | Stanley, Jr. ........................... 422/24 X |
| 5,247,178 | 9/1993 | Ury et al. .............................. 422/24 X |
| 5,417,852 | 5/1995 | Furness, Jr. et al. .................... 210/188 |
| 5,612,001 | 3/1997 | Matschke ............................... 422/24 X |

*Primary Examiner*—E. Leigh McKane
*Attorney, Agent, or Firm*—Bazerman & Drangel, PC

[57] ABSTRACT

A germicidal water cleansing apparatus having an ellipsoid chamber which contains UV lamps along the major axis of the ellipsoid. Each of the ends of the ellipsoid has an opening to allow the entry and exit of a liquid. The chamber is formed from an ultraviolet reflective material such as spun aluminum to allow uniform dispersion of the ultraviolet radiation throughout the chamber. The liquid is drawn through the chamber at a rate to assure a high kill rate of microorganisms present in the liquid.

11 Claims, 2 Drawing Sheets

APPARATUS FOR GERMICIDAL CLEANSING OF WATER

This application is a continuation-in-part of Ser. No. 08/538,447, filed Oct. 3, 1995, now U.S. Pat. No. 5,612,001, issued Mar. 18, 1997.

BACKGROUND OF THE INVENTION

Bacteria or other microorganisms permeate the air we breath and the water we drink. Much effort has gone into trying to limit or destroy atmospheric or water-borne pathogens. It has long been recognized that pathogens can be destroyed if they are irradiated with ultraviolet (UV) light of a wavelength of 253.7 nanometers. In order for the UV light to kill microorganisms, and particularly pathogens, the rays must directly strike them.

For example, U.S. Pat. No. 4,714,870 discloses a fluorescent lamp emitting germicidal ultraviolet radiation for use in a water purifying apparatus. Similarly, U.S. Pat. No. 5,484,358 to Woodward, discloses the use of a UV fixture for germicidal purposes in a water purifier and dispenser. U.S. Pat. No. 4,752,401 discloses the use of a UV lamp in a water treatment system for swimming pools and portable water, wherein the water passes through a stainless steel chamber having a UV light source located within the chamber. The chamber is cylindrical in formation having transverse ends. There is no effort to shape the stainless steel chamber to assure that there is even distribution of the ultraviolet radiation throughout the chamber. Stainless steel itself is of relatively low reflectivity for UV light and, thus, would not, by its nature, act to ensure uniformity of the UV radiation throughout the chamber or the maintenance of a high level.

SUMMARY OF THE INVENTION

It is an object of the present invention to provide an ultraviolet light chamber for processing water which combines both optics and water-flow techniques to kill microorganisms present in the water.

It is a further object of the present invention to cause all water flowing throughout the present invention to be exposed at a uniform constant rate to high levels of ultraviolet radiation.

It is a further object of the present invention to do so with no ultraviolet exposure to humans.

It is a further object of the present invention to filter the water to minimize water-borne particulates, thereby raising the illumination level throughout the serviceable UV lamp life.

In the present invention, water is circulated through and the attended water-borne bacteria and viruses are drawn into a chamber designed to achieve uniform dispersal of ultraviolet rays throughout. The microorganisms present are exposed to high, uniform intensity ultraviolet rays. Filters remove particulates, help to prevent scale accumulation and organic deposits, and keep ultraviolet lamps efficient and operating at design specifications throughout the life of the machine.

The chamber is formed from spun aluminum. The chamber cross-section is that of an ellipse, i.e., it is ellipsoid, with the major axis of the ellipse being the direction through which the water is drawn. Such elliptical design causes uniform irradiation as the water passes through the chamber.

The chamber has an opening at each end to allow water to pass through the chamber. In one embodiment, the water fills the chamber and in a second embodiment the water passes through the chamber in a tube formed of a material which is transparent to UV light at germicidal wavelengths. The design of the chamber assures that ultraviolet energy is uniformly distributed throughout, any isolated point in the chamber having an identical energy level as any other point. The chamber is sized to allow the water to flow at the desired rate through the chamber while assuring the desired kill rate, i.e., exposure to a sufficient UV radiation at an intensity and for a sufficient time to reach the desired germicidal kill ratio.

The chamber is made from aluminum or light material which is highly reflective to the UV radiation. The primary function of the chamber is to enhance the irradiation quantum performance of a germicidal ultraviolet source located within the chamber through which the water flows. The germicidal ultraviolet source kill factor of water-borne microorganism passing through the chamber is a function of the radiation intensity, volume of water and flow rate. The chamber is positioned at any attitude from vertical to horizontal with respect to the longitudinal axis. The fluid flows under sufficient pressure to fill the chamber at the selected flow rate. The fluid enters the chamber at one extremity of the chamber, i.e., at the portion of smallest radii of curvature of the chamber and leaves at the opposite end. The ellipsoid configuration of the chamber, in combination with its use of highly UV reflective material in its construction, assures that the radiation will be retained within the chamber reaching a much higher steady state level than a cylindrical enclosure made from a non-UV reflective material and assures that this level of radiation will be evenly disbursed throughout the chamber.

The chamber, formed of equal halves separated at the greatest diameter, may either be formed by spinning, stamping or other cold working methods or may be molded of glass, plastic, or similar materials and a layer of reflective material, such as aluminum, magnesium, or the like, by a means such as vacuum depositing, spraying, electrostatic processing or impregnation. Due to the nature of the ellipsoid chamber, the chamber is scalable in size for uses such as sterilizing water in clinical use, such as in dialysis and blood equipment, to large-scale potable water sterilization and the disinfection of secondary effluents in water recovery. Filters are used at the beginning of the water flow to remove water-borne particulates to thereby reduce scale accumulation and organic deposits, preventing contamination of the chamber effecting luminescence and reflectance. In one embodiment, the chamber structure prevents the loss of lamp output due to either scale accumulation or organic deposit.

BRIEF DESCRIPTION OF THE DRAWINGS

The invention will be described by way of example with reference to the accompanying drawings wherein.

DETAILED DESCRIPTION OF THE PREFERRED EMBODIMENTS

Figure 1:
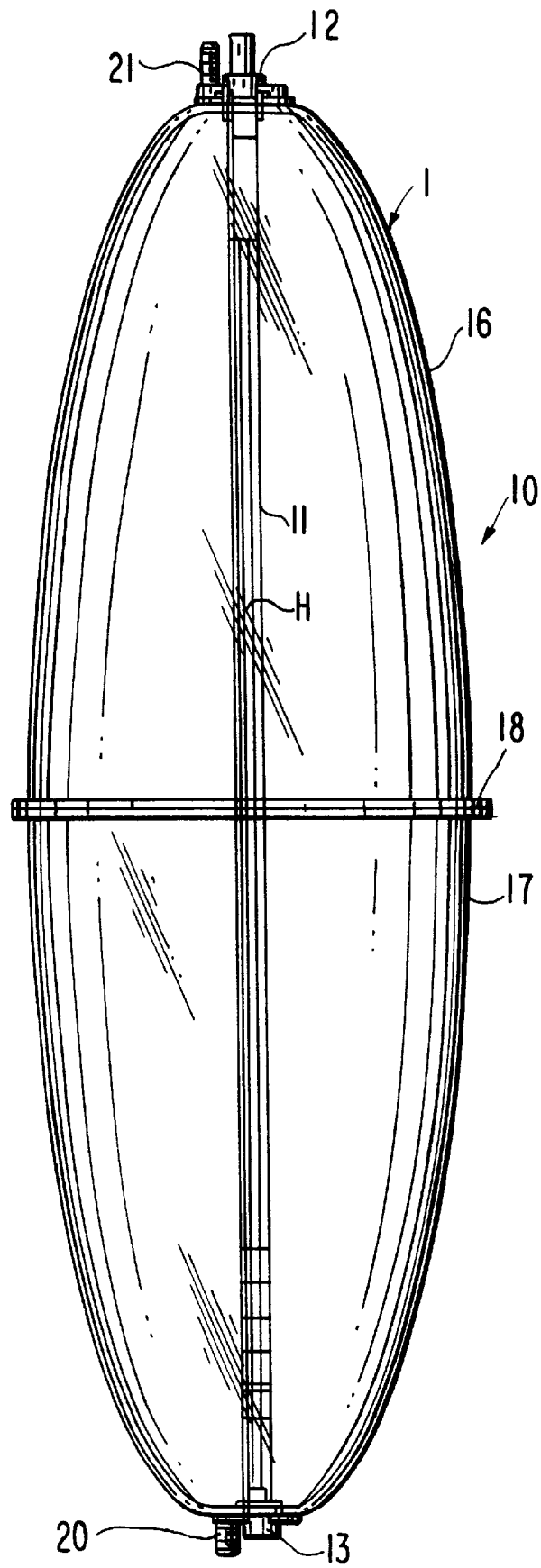
FIG. 1 is a schematic diagram of a germicidal water cleaning chamber of the present invention.

The present invention is an ultraviolet water purification system 10 in which water is passed through ultraviolet radiation in which the water is irradiated with ultraviolet light at a germicidal "far" wavelength, i.e., at 253.7 nanometers. Because of the unique construction of the chamber 1 in which the water is irradiated, the radiation is uniform throughout the chamber which reaches a steady state in operation at an extremely high radiation level. The chamber is positioned at any attitude from vertical to horizontal. The fluid in the chamber is under sufficient pressure to fill the chamber at the selected flow rate. Chamber 1 is ellipsoid in configuration. UV source 14 may consist of one or more UV lamps of standard construction. They are mounted in a water tight sheath 11 made of quartz or other UV transparent material. Sheath 11 is mounted at brackets 12 and 13 which have electrical sockets (not shown) mounted therein, sealed such that water passing through the chamber 1 cannot enter the quartz sheath 11 or otherwise come in contact with the UV source. The UV sources are mounted in electrical sockets mounted in the brackets 12 and 13. Water enters through fitting 20 into the chamber 1. Fitting 20 may be integral with bracket 13. A filter, not shown, may be positioned at fitting 20 to remove particles. The water exits through fitting 21 at the other end of the ellipsoid chamber 1 which may be integral with bracket 12. The chamber 1 may be formed from two sections 16 and 17 which are fitted together at 18 to form a water tight seal. Gaskets and other sealing means may be used at brackets 12, 13, fittings 20, 21 and at 18 to ensure a water tight seal throughout.

Chamber 1 is ellipsoid in shape made of UV irradiation reflective walls. The ray path of an ellipse, i.e., the cross-section of an ellipsoid along its major axis, is the perfect reflector, compensating for reflective angles as a function of distance. Accordingly, the light emitted by the UV source is evenly spread throughout the chamber and is evenly disbursed throughout the length of chamber 1. Any point in chamber 1 receives the same quantity of UV light in all directions as any other point within the chamber. Since the walls of the chamber are made of a highly UV reflective material, such as spun aluminum, the greatest part of the energy generated by the UV lamps 14 is reflected back into the chamber rather than being absorbed by the walls of the chamber. Accordingly, a very high level of steady state UV radiation is reached in the chamber even in comparison to the UV source 14. Because the chamber 1 is ellipsoid it has a long exposure path for extended UV radiation treatment of the water passing through the chamber 1.

In general, the UV reflectance efficiency of a metal is limited inversely to its atomic weight, for example:

| METAL | REFLECTANCE EFFICIENCY | ATOMIC NUMBER |
| --- | --- | --- |
| Aluminum | 88% | 26.98 |
| Chromium | 45% | 51.99 |
| Nickel | 38% | 58.71 |
| Silver | 22% | 107.86 |

Aluminum is a material which is both highly reflective and practical for construction of a chamber. Magnesium also would be suitable for certain applications.

Since the kill rate is dependent both on the intensity and length of exposure to the UV radiation, if the UV radiation were not evenly disbursed throughout the chamber, the amount of exposure and, thus, the kill rate would vary across the chamber 1. Here, due to the design of chamber 1 and the position of the light source longitudinally along chamber 1 parallel to extended main axis of the ellipsoid forming the longitudinal cross-section of chamber 1. The kill rate is both high and constant for all water passing through the extended water path through chamber 1.

The total energy in chamber 1 can be calculated based upon UV lamps 14 output. For example, commercially available UV lamps specify an output of 13.8 watts (i.e., 13.8 joule/sec.) of ultraviolet energy. After a period of initial use of several hundred hours, there will be an output degradation of 20%. Since the output of the UV lamp is retained within chamber 1, aside from the amount absorbed by the walls of the chamber, calculating the power being delivered to the chamber is relatively simple. If six (6) such lamps are placed within chamber 1, the total power being delivered to chamber 1 would equal approximately 72.8 watts (72.8 joules/sec.) of UV radiation or after degradation, approximately 65 watts or 65 joules/sec. In the spun aluminum chamber 1 the present invention, approximately 10% of that energy is absorbed by the internal structural components, leaving an average energy input of 58.5 watts (58.5 joules/sec.) into the chamber. This tends to result in a build up of radiation in the chamber. Such build up is necessary to compensate for normal losses to water absorption. Accordingly, it is extremely important that a steady state at high radiation level be reached within the chamber to compensate for such losses.

The fittings 20 and 21 may be curved on the inner surface so as to continue the ellipsoid surface of the chamber and, therefore, promote the uniform irradiation within the chamber.

Figure 2:
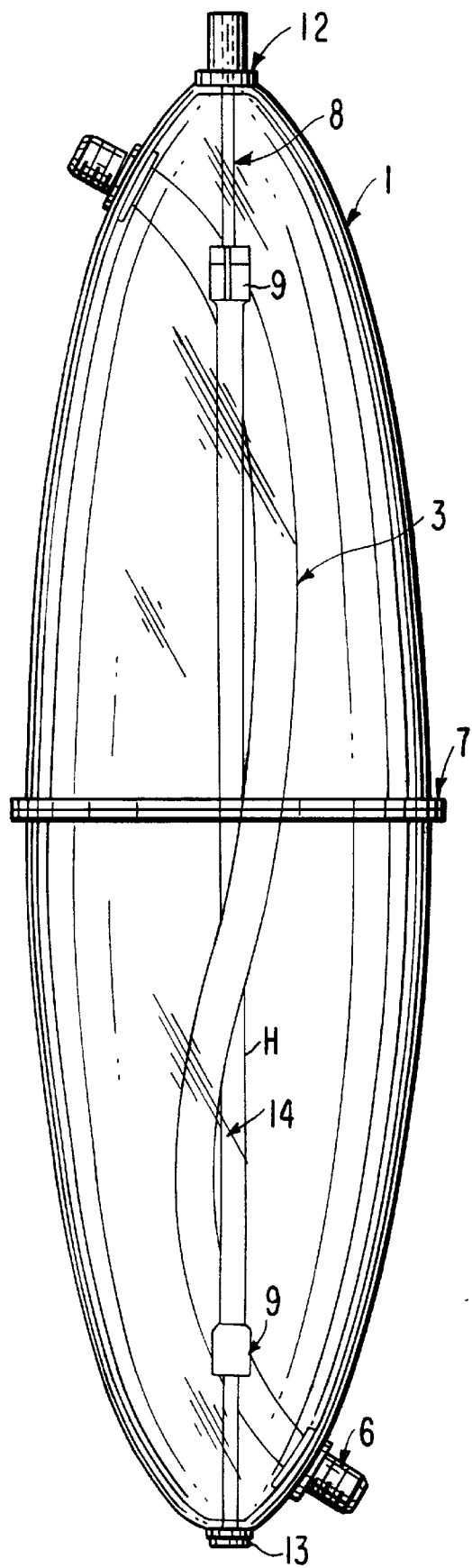
FIG. 2 is a second embodiment of the germicidal water cleaning chamber of the present invention.

FIG. 2 shows a second embodiment of the present invention having a similar construction of the chamber 1 with the UV source 14 longitudinally centered in the chamber 1 with electrical conduit brackets 12 and 13 mounted at each end. A brace tube 8 holds the lamp in position and contains the wiring for the UV source, and is attached to entry fittings at each end of chamber 1 and to the sockets 9 holding the UV light at each end. A quartz helical tube 3 extends through the chamber around the UV source. There is a clearance or space between the quartz helical tube 3 and the UV source 14. The quartz helical tube 3 will complete a minimum of one or more complete revolutions around the UV source 14 in the chamber. As in the previous designs, the UV source reaches a steady state based in part of the reflectivity of the walls of the chamber and in part of the ellipsoid shape of the chamber. The radiation is uniform throughout the chamber and irradiates the liquid passing through the quartz helical tube 3. The quartz helical tube 3 will have fittings at either end 6 for attachment to piping, hosing or the like, for conveying fluid through the chamber. The steady-state level of irradiation is at a higher value in this construction than the first embodiment since the chamber is not completely filled with fluid. Further, the quartz liquid carrying helix wall of this embodiment requires only sufficient strength to contain fluids and is thinner than the construction of the central sheath of the first embodiment which requires greater structural weight and cross section. The helical tube 3 absorbs less irradiation energy than the sheath 11. Since the UV source 14 and the fluid are separated, the UV source is not cooled by the fluid which can effect its efficiency in producing UV irradiation. Such separation of the UV source 14 and the fluid prevents scale accumulations and organic deposits on the source 14 which may adversely effect irradiation intensity. This construction also allows for chemical cleaning and gas environmental purges.

Instead of a longitudinal UV lamp, a xenon flash UV source can be centrally located to employ the steady-state irradiation provisions of the chamber. Alternatively, one or more lasers may be selectively positioned to fire into the chamber using the configuration of the chamber to disperse this energy.

The same construction can be used with a number of different fluids including water and the size of the chamber can be varied to suit flow volume and irradiation dose needs.

While the invention has been described as having a preferred design, it is understood that it is capable of further modification, uses and/or adaptations of the invention following in general principle of the invention and including such departures from the present disclosure as come within known or customary practice in the art to which the invention pertains, as may be applied to the central figures hereinabove set forth and fall within the scope of the invention of the limits of the appended claims.

What is claimed is:

1. An apparatus for germicidal cleansing of a liquid comprising:

an ellipsoid irradiation chamber;

said chamber having a first opening to allow a liquid to enter the chamber and second opening to allow a liquid to leave the chamber;

an ultraviolet light source positioned to introduce UV irradiation into the chamber;

the internal wall of the chamber is made from an ultraviolet reflective material; and the wall of the ellipsoid chamber directs ultraviolet light incident upon the wall of the chamber uniformly throughout the chamber such that the energy in the chamber accumulates over time to reach a uniform steady state energy level throughout the chamber greater than that emitted by the UV source.

2. An apparatus according to claim 1 wherein the first and second openings are located at either end of the ellipsoid chamber along its major axis.

3. An apparatus according to claim 2 wherein the chamber is formed from spun aluminum.

4. An apparatus according to claim 2 wherein a UV transparent conduit is positioned between the first opening and the second opening through which the liquid to be exposed passes.

5. An apparatus according to claim 4 wherein the conduit has a helical configuration which spirals through the chamber.

6. An apparatus according to claim 4 where the UV source is not in direct contact with the liquid and thereby not exposed to cooling effect of the liquid, scale accumulation or organic deposits.

7. An apparatus according to claim 4 wherein the outer surface of the UV transparent conduit is accessible for chemical cleaning and gas environmental purge.

8. An apparatus according to claim 4 where the steady-state exposure value is constant throughout the chamber.

9. An apparatus according to claim 2 wherein a filter is positioned before the first opening in the chamber to filter the liquid which is allowed to enter the chamber.

10. An apparatus according to claim 2 wherein the UV light source is a UV lamp positioned along the major axis of the chamber.

11. An apparatus according to claim 2 where the UV source is a UV laser which fires into the chamber.

* * * * *